United States Patent [19]

Haeck et al.

[11] Patent Number: 4,939,136
[45] Date of Patent: Jul. 3, 1990

[54] NEW ANELLATED INDOLE DERIVATIVES

[75] Inventors: Hans H. Haeck; Derk Hamminga; Ineke Van Wijngaarden; Wouter Wouters, all of Weesp, Netherlands

[73] Assignee: Duphar International Research B.V., Weesp, Netherlands

[21] Appl. No.: 210,976

[22] Filed: Jun. 24, 1988

[30] Foreign Application Priority Data

Jun. 29, 1987 [NL] Netherlands ............... 8701516
Mar. 16, 1988 [NL] Netherlands ............... 8800643

[51] Int. Cl.⁵ .................. C07D 521/00; C07D 403/06
[52] U.S. Cl. .................... 514/183; 514/214; 514/224.5; 514/229.5; 514/284; 514/397; 540/477; 540/520; 544/14; 544/99; 546/72; 548/336
[58] Field of Search ............ 546/72, 18; 514/284, 514/397, 214, 183, 276, 224.5, 229.5; 548/336; 540/576, 480, 543, 466, 477, 520; 544/14, 99

[56] References Cited

PUBLICATIONS

*Chemical Abstracts*, Birch et al., (61) 10725(a), 1964.

*Primary Examiner*—Mary C. Lee
*Assistant Examiner*—M. S. Howard
*Attorney, Agent, or Firm*—Stevens, Davis, Miller & Mosher

[57] ABSTRACT

The invention relates to new anellated indole derivatives of general formula 2,

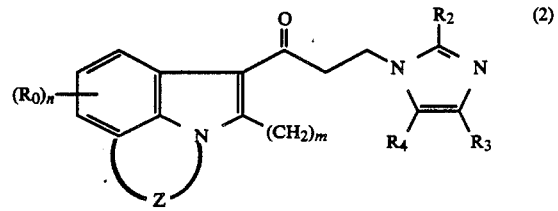

wherein p1 $R_0$ is alkyl or alkoxy having 1–4 C-atoms, phenylalkoxy having 1–3 C-atoms in the alkoxy group, hydroxy, halogen, trifluoromethyl, trifluoromethoxy, trifluoromethylthio, or a group $R_7S(O)_p$, wherein $R_7$ is alkyl having 1–4 C-atoms and p has the value 0, 1 or 2, or $R_0$ is a group $R_8R_9N$, $R_8R_9N$—CO—$CH_2$— or $R_8R_9$—N—CO wherein $R_8$ and $R_9$ are hydrogen or alkyl having 1–4 C-atoms or $R_8R_9N$ forms a saturated 5- or 6-membered ring and n has the value 0, 1 or 2, Z together with the carbon atom and nitrogen atom to which Z is bound and the intermediate carbon atom, forms a heterocyclic group consisting of 5–8 ring atoms, in which, in addition to the nitrogen atom already present, a —CO—group or a second hetero atom from the group N, O, S, S-O or $SO_2$ may be present, which ring may be substituted with 1–3 alkyl groups having 1–4 C-atoms, a phenyl group or a spiroalkyl group ($C_2$–$C_5$), or which ring may be anellated with a saturated or non-saturated carbocyclic or heterocyclic ring which consists of 5- or 6-ring atoms and which may be substituted with halogen, alkyl or alkoxy having 1–4 C-atoms, and m has the values 1–5,
one of the groups $R_2$, $R_3$ and $R_4$ is hydrogen, alkyl having 1–6 C-atoms, cycloalkyl having 3–7 C-atoms, alkenyl having 2–6 C-atoms or phenylalkyl having 1–3 C-atoms in the alkyl group, and the two other groups independently of each other are hydrogen or alkyl having 1–6 C-atoms, and the pharmaceutically acceptable acid addition salts thereof. These compounds are strong and selective antagonists of "neuronal" 5-hydroxytryptamine (5-HT) receptors, and have a considerably longer-lasting effect and lower toxicity in comparison with related known compounds.

2 Claims, No Drawings

NEW ANELLATED INDOLE DERIVATIVES

The invention relates to a group of new anellated indole derivatives which are substituted with an imidazolylmethyl group, to the preparation thereof, and to compositions which comprise at least one of these compounds as an active substance.

It is known from Belgian Patent Specification No. 901576 and European Patent Application No. 86305671.9 (publication no. 0210840) that carbazolone compounds of formula 1

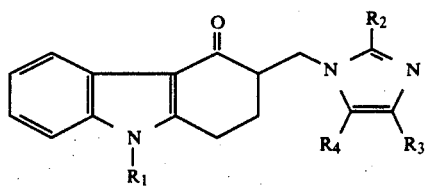

wherein $R_1$ is hydrogen, alkyl having 1–10 C-atoms, cycloalkyl having 3–7 C-atoms, alkenyl having 3–6 C-atoms, phenyl or phenylalkyl (1–3 C in the alkyl group), or a group $CO_2R_5$, $COR_5$, $CONR_5R_6$ or $SO_2R_5$, respectively (wherein $R_5$ and $R_6$ may inter alia be alklyl or cycloalkyl), and wherein one of the groups $R_2$, $R_3$ and $R_4$ is hydrogen, alkyl (1–6 C), cycloalkyl (3–7 C), alkenyl (2–6), or phenylalkyl (1–3 C in the alkyl group), and the two other groups may be hydrogen or alkyl (1–6 C), are strong and selective antagonists of "neuronal" 5-hydroxytryptamine (5-HT) receptors.

It has surprisingly been found that compounds of formula 2

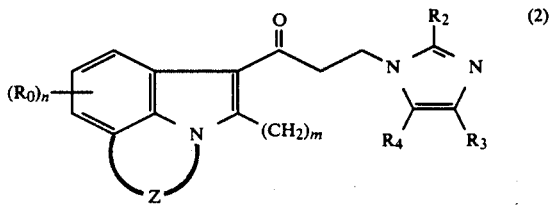

wherein $R_0$ is alkyl or alkoxy having 1–4 C-atoms, phenylalkoxy having 1–3 C-atoms in the alkoxy group, hydroxy, halogen, trifluoromethyl, trifluoromethoxy, trifluoromethylthio, or a group $R_7SO(O)_p$, wherein $R_7$ is alkyl having 1–4 C-atoms and p has the value 0, 1 or 2, or $R_0$ is a group $R_8R_9N$, $R_8R_9N—CO—CH_2—$ or $R_8R_9—N—CO$ wherein $R_8$ and $R_9$ are hydrogen or alkyl having 1–4 C-atoms or $R_8R_9N$ forms a saturated 5- or 6-ring and n has the value 0, 1 or 2, Z together with the carbon atom and nitrogen atom to which Z is bound and the intermediate carbona atom, forms a heterocyclic group consisting of 5–8 ring atoms, in which, in addition to the nitrogen atom already present, a —CO—group or a second hetero atom from the group N, O, S, S—O or $SO_2$ may be present, which ring may be substituted with 1–3 alkyl groups having 1–4 C-atoms, a phenyl group or a spiroalkyl group ($C_2$–$C_5$), or which ring may be anellated with a saturated or non-saturated carbocyclic or heterocyclic ring which constists of 5- or 6-ring atoms and which may be substituted with halogen, alkyl or alkoxy having 1–4 C-atoms, and m has the values 1–5, one of the groups $R_2$, $R_3$ and $R_4$ is hydrogen, alkyl having 1–6 C-atoms, cycloalkyl having 3–7 C-atoms, alkenyl having 2–6 C-atoms or phenylalkyl having 1–3 C-atoms in the alkyl group, and the two other groups independently of each other are hydrogen or alkyl having 1–6 C-atoms, and the pharmaceutically acceptable acid addition salts thereof have similar but considerably longer-lasting effect and a lower toxicity than the known compounds of formula 1.

Suitable acid with which the compounds of formula 2 according to the invention can form pharmaceutically acceptable acid addition salts are, for example, hydrochloric acid, sulphuric acid, phosphoric acid, nitric acid, and organic acids, for example, citric acid, fumaric acid, maleic acid, tartaric acid, acetic acid, benzoic acid, p-toluenesulphonic acid, methanesulphonic acid, and the like.

The carbon atom to which the imidazolylmethyl group is bound is a centre of chirality. Also chirality can occur when the rings are substituted. Both the racemates and the individual enantiomers of compounds of formula 2 belong to the invention.

The antagonistic activity of the compounds of formula 2 on the response induced by 5-HT or 2-methyl-5-HT was determined and measured in the Bezold-Jarish reflex test in rats. The compounds appeared to have a good antagonistic activity in this test when administered in an intravenous dose of less than 100 μg/kg.

The affinity for "neuronal" 5-HT receptors has also been determined and measured by means of the displacement of ($^3$H) GR 38032 F in neuroblastoma cells. In this test $pK_i$-values of more than 7.0 have been found.

On the basis of the antagonistic activity on this type of 5-HT receptors, the compounds may be used for the treatment of symptoms which are caused by over-stimulation of the said receptors (a) in the gastrointestinal system (nausea and vomitting as a result of exogenic factors, for example, cancer therapy, or endogenic factors, for example, stasis of the stomach and migraine), ulcer, dyspepsia, etc., or (b) in the central nervous system (hallucinations, delusions, manias, anxiety, pain, vigilance improving, etc.), or (c) in the cardio-vascular system, for example, spasms of the vessels, arrhythmias, etc., or (d) in the respiratory system (including nasal disorders and disorders in the bronchi and lungs).

The compounds according to the invention and their salts can be brought into forms suitable for administration, for example, pills, tablets, coated tablets, capsules, powders, injection liquids and the like by means of method conventionally used for this purpose and while using suitable auxiliary agents, for example, solid or liquid carrier materials.

The dosage in which the compounds according to the invention may be used depend on the severity and the nature of the disease to be treated and on the way of administration. As a rule, the dosage will be between 0.05 and 20 mg, preferably between 0.1 and 10 mg of active substance daily.

The compounds according to the invention may be prepared in a manner known for analogous compounds. Suitable methods of preparing this type of compounds are described, for example, in the above-mentioned European Patent Application published under number 0210840.

In particular the compounds of formula 2 can be obtained in a good yield by reaction of a compound of formula 3

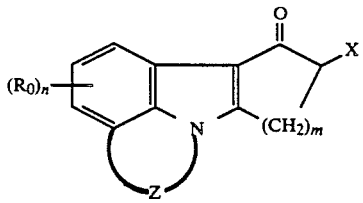

(3)

wherein R₀, n, m and Z have the above meanings, and X is a reactive group, preferably the group =CH₂ or —CH₂N(CH₃)₂, with an imidazole compound of formula 4

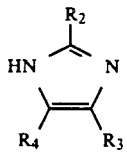

(4)

or a salt thereof, wherein R₂, R₃ and R₄ have the above-mentioned meanings.

The reaction is preferably carried out in a suitable solvent, for example, water, alcohol, dimethylformamide, etc. at temperatures between 20° C. and 150° C.

The starting compounds of formula 3 to be used in this reaction can be obtained, for example, by reaction of a compound of formula 5

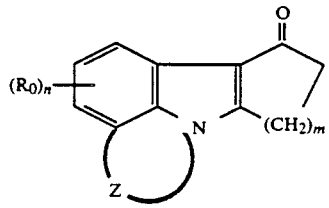

(5)

wherein R₀, n, m and Z have the above-mentioned meanings, with formaldehyde and dimethylamine hydrochloride, preferably in an organic solvent, for example, acetic acid or alcohol, while heating.

The starting substances of formula 5 can be prepared in a manner for analogous compounds by oxidation of a compound of formula 6

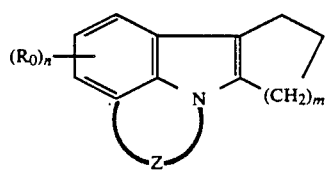

(6)

wherein R₀, n, m, and Z have the above meanings, with a suitable oxidation agent, for example, 2,3-dichloro-5,6-dicyano-1,4-benzoquinone (DDQ) or selenium dioxide preferably in a suitable solvent, for example, water, tetrahydrofuran or dioxan. In particular the starting substances of formula 5 can be obtained in a good yield by oxidation with DDQ of the analogous compounds of formula 6 in tetrahydrofuran and water at temperatures between —° and 20° C. as described for similar compounds in J. Org. Chem. 42, (1977), p. 1213. The compounds of formula 6 are known compounds or can be obtained analogously to known compounds.

Further the starting substances of formula 5 can be obtained in a manner known per se by ring closure of compounds of formula 7

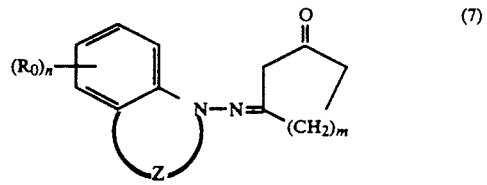

(7)

wherein R₀, n, m and Z have the above-mentioned meanings. This ring closure reaction may be carried out, for example, by boiling in an organic solvent, for example, acetic acid in the presence of an acid catalyst, for example, concentrated hydrochloric acid or sulphuric acid.

The compounds of formula 7 are known compounds or can be obtained analogously to known compounds.

The invention will now be described in greater detail, by way of example, with reference to the ensuing specific examples.

EXAMPLE I 4,5,6,8,9,10-hexahydro-10-[(2-methyl-1H-imidazol-1-yl)methyl]-11H-pyrido-[3,2,1-jk]-carbazol-11-one (a) Preparation of a compound of formula 7

A mixture of 46.3 g (313 mmol) of 1-amino-1,2,3,4-tetrahydroquinoline and 38 g (329 mmol) of cyclohexanedione-1,3 in 150 ml of absolute ethanol was boiled for 1 hour while stirring. The reaction mixture was then evaporated to dryness and the residue was dissolved in 100 ml of methanol. 200 ml Of ethyl acetate were added to the resulting solution, after which the mixture was left to crystallize. After leaving to stand overnight at 0° C. and sucking off, 48.3 g of pure product were obtained. Another 19,8 g of product were recovered from the mother liquor. Overall yield 68.1 (90%) having a melting-point of 153°–156° C.

(b) Preparation of a compound 5 by ring closure of a compound 7

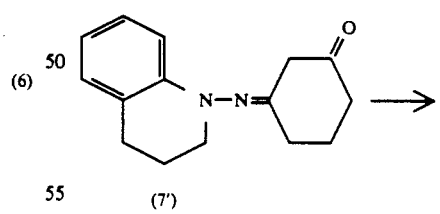

(7')

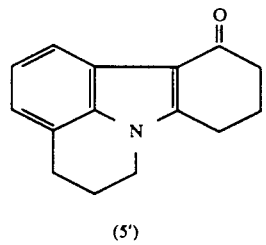

(5')

66.1 g of the hydrazone 7' obtained in (a) were mixed with 600 ml of acetic acid and 100 ml of concentrated hydrochloric acid. This mixture was boiled while stirring under an atmosphere of nitrogen for 1 hour. After leaving to stand overnight the mixture began to crystallize. After leaving to stand one day at room temperature and overnight at 0° C., sucking off, washing with ethanol and water, and drying, 23.5 g of product were obtained (melting-point 173°–174° C.). Another 13.1 g of pure product were obtained from the mother liquor after chromatography. Overall yield 36.6 (60%).

(c) Preparation of compound 3 from compound 5

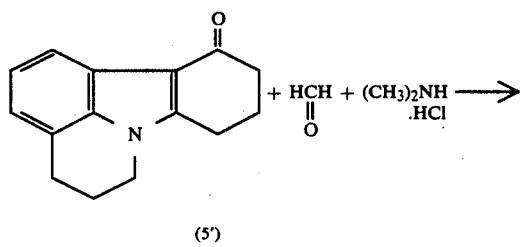

(5')

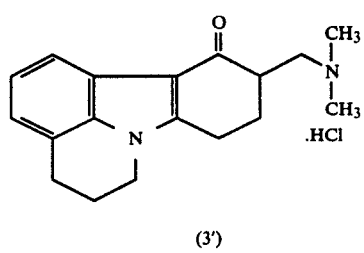

(3')

6.75 (30 mmol) of the ketone of formula 5' were mixed with 1.8 g (60 mmol) of paraformaldehyde, 5.4 g (66 mmol) of dimethylamine hydrochloride and 90 ml of acetic acid, and the mixture was heated in a bath of 100° C. for 3 hours. After evaporating to dryness the residue was rendered alkaline with 2N NaOH and taken up in water, shaken with dichloromethane, evaporated to dryness and chromatographed. After evaporating the good fraction 5.1 g of the free base of compound 3' were obtained. This base was dissolved in 25 ml of boiling ethanol to which 2 ml of concentrated hydrochloric acid were added. The crystallised hydrochloride 3', after leaving to stand overnight at 0° C., was sucked off, washed with ethanol and dried, 5.1 g (53%) of product being obtained (melting-point) 208°–209° C.).

(d) Reaction of a compound 3 with a compound 4

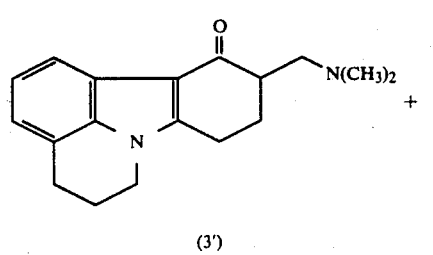

(3')

+

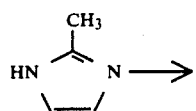

-continued

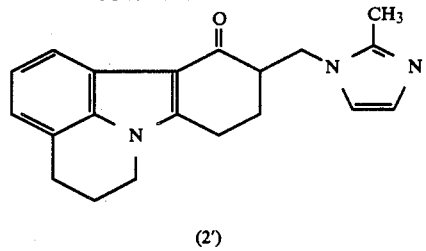

(2')

3.2 g (10 mmol) Of the salt 3' obtained according to (c) were mixed with 2.5 g (30 mmol) of 2-methylimidazole and 30 ml of water. The mixture was boiled for 20 hours under nitrogen while stirring. After cooling, while stirring, the product crystallised. After cooling to 0° C., sucking off, drying and chromatographing, 2.8 g (87%) of the desired compound of formula 2' were obtained (melting-point 183°–184° C.).

EXAMPLE II (a)
4H,8H-5,6,9,10,11,12-hexahydro-cyclohepta-[4,5]-pyrrolo[3,2,1-ij]-quinoline-12-one A solution of 25 g of 2,3-dichloro-5,6-dicyano-1,4-benzoquinone (110 mmol) in 250 ml of tetrahydrofuran is added dropwise in 1.5 hours while stirring and at −5°–0° C. to a solution of 12.2 g of 4H,8H-5,6,9,10,11,12-hexahydrocyclohepta-[4,5]-pyrrolo-[3,2,1-ij]-quinoline (54 mmol) in 500 ml of tetrahydrofuran and 50 ml of water. After everything has been added dropwise, stirring is continued for another 2–3 hours at 0° C. Approximately 200 ml of silicagel are then added and the whole is evaporated to dryness. After chromatographing twice and after evaporating the good fraction. 2.7 g of product (21%) are obtained (melting-point 141°–143° C.).

(b)
4H,8H-5,6,9,10,11,12-hexahydro-11-](dimethylamino)-methyl]-cyclohepta-[4,5]-pyrrolo-[3,2,1-ij]-quinolin-12-one.hydrochloride 2.7 g (11.3 mmol) of 4H,8H-5,6,9,10,11,12-hexahydrocyclohepta-[4,5-pyrrolo-[3,2,1-ij]-quinolin-12-one are mixed with 0.68 g (22.6 mmol) of paraformaldehyde, 2.0 g (25 mmol) of dimethylamine hydrochloride and 50 ml of acetic acid, and the mixture is heated in a bath of 100° C. for 1 hour. After evaporting to dryness the residue is rendered alkaline with 2N NaOH, extracted with dichloromethane, evaporated to dryness, and chromatographed. After evaporating the good fraction, 2.37 g of the free base are obtained. This base is dissolved in 7.5 ml of absolute ethanol to which 1 ml of concentrated hydrochloric acid is added. The crystallised hydrochloride, after having been left to stand overnight at 0° C., is sucked off, washed with little cold absolute ethanol and dried. Yield 2.0 g (53%). Metlting-point 198°–199° C. (decomposition).

(c)
4H,8H-5,6,9,10,11,12-hexahydro-11-[(2-methyl)-1H-imidazol-1-yl)-methyl]-cyclohepta-[4,5]-pyrrolo-[3,2,1-ij]-quinolin-12-one 2.0 g (6 mmol) of 4H,8H-5,6,9,10,11,12-hexahydro-11-[(dimethylamino)-methyl]-cyclohepta-[4,5]-pyrrolo-[3,2,1-ij]-quinolin-12-one hydrochloride are mixed with 1.6 g (20 mmol) of 2-methylimidazole, 25 ml of water and 25 ml of n-propanol. The mixture is boiled under nitrogen for 48 hours while stirring. After cooling, the reaction mixture is poured out in 2N NaOH and extracted with dichloromethane, evaporated and chromatographed. After evaporating the good fraction, 1.78 g (89%) of the desired compound are obtained. Metlting-point 159°–161° C.

The compounds of formula 2 indicated in the following table have been prepared according to the method of Example I and II repsectively.

was cooled to room temperature while stirring. After a night at room temperature the solid substance was sucked off, washed with cold DMF/water (2:1), with absolute ethanol, with ether, and dried. Yield 14.6 g.

This crystallisation procedure was repeated twice using 25 ml of the (2:1) mixture DMF and water per 1 g of the above salt. Yield: 7.9 g having a melting point of 155°–157° C. (decomposition), and $[\alpha]_D^{25} = +76°$ (c=0.3; methanol).

A solution of 1.6 ml of acetyl chloride in 15 ml of

TABLE

| comp. no. | $(R_0)_n$ | Z | m | $R_2$ | $R_3$ | $R_4$ | salt | m.p. (°C.) | method of example |
|---|---|---|---|---|---|---|---|---|---|
| 1 | H | —CH$_2$CH$_2$— | 2 | CH$_3$ | H | H | base | 226–227 | I |
| 2 | H | —CH$_2$—C(CH$_3$)— | 2 | CH$_3$ | H | H | base | 190–191 | I |
| 3 | H | —CH$_2$—CH$_2$—CH$_2$— | 2 | H | H | H | base | 217–218 | I |
| 4 | H | —CH$_2$—CH$_2$—CH$_2$— | 2 | C$_2$H$_5$ | H | H | HCl | 165–168 | I |
| 5 | H | —CH$_2$—CH$_2$—CH(CH$_3$)— | 2 | CH$_3$ | H | H | base | 149–152 | I |
| 6 | H | —O—CH$_2$—CH$_2$— | 2 | CH$_3$ | H | H | base | 230–231 | I |
| 7 | H | —S—CH$_2$—CH$_2$— | 2 | CH$_3$ | H | H | base | 213–215 | I |
| 8 | 1-Cl | —CH$_2$—CH$_2$—CH$_2$— | 2 | CH$_3$ | H | H | base | 252–255 | I |
| 9 | 2-F | —CH$_2$—CH$_2$—CH$_2$— | 2 | CH$_3$ | H | H | base | 184–185.5 | I |
| 10 | 2-Cl | —CH$_2$—CH$_2$—CH$_2$— | 2 | CH$_3$ | H | H | base | 201–204 | I |
| 11 | 2-OCH$_3$ | —CH$_2$—CH$_2$—CH$_2$— | 2 | CH$_3$ | H | H | base | 189.5–191.5 | I |
| 12 | 3-F | —CH$_2$—CH$_2$—CH$_2$— | 2 | CH$_3$ | H | H | base | 219–222 | I |
| 13 | 3-Cl | —CH$_2$—CH$_2$—CH$_2$— | 2 | CH$_3$ | H | H | base | 190.5–192.5 | I |
| 14 | H | —(CH$_2$)$_4$— | 2 | CH$_3$ | H | H | base | 188.5–191 | I |
| 15 | H | —CH$_2$—CH$_2$—(o-tolyl) 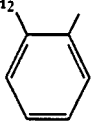 | 2 | CH$_3$ | H | H | base | foam | I |
| 16 | H | —(CH$_2$)$_5$— | 2 | CH$_3$ | H | H | HCl | 231.2–231.6 | I |
| 17 | H | —CH$_2$—CH$_2$—CH$_2$ | 3 | CH$_3$ | H | H | base | 159–151 | II |
| 18 | H | —(CH$_2$)$_4$— | 3 | CH$_3$ | H | H | base | 130–131 | II |
| 19 | H | —CH$_2$—CH$_2$—(o-tolyl) 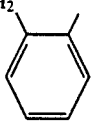 | 3 | CH$_3$ | H | H | HCl | 221.5–223.5 | II |
| 20 | H | —CH$_2$CH$_2$—CH$_2$— | 4 | CH$_3$ | H | H | base | 180–182 | II |

EXAMPLE III (−)-4,5,6,8,9,10-hexahydro-10-[(2-methyl-1H-imidazol-1-yl)methyl-11H-pyrido-[3,2,1-jk]-carbazol-11-one, hydrochloride A solution of 12.5 g of (+)-di-p-toluyl-D-tartaric acid monohydrate in 125 ml of warm methanol was added to a solution of 9.8 g of (R, S)-4,5,6,8,9,10-hexahydro-10-[(2-methyl-1H-imidazol-1-yl)methyl]-11H-pyrido-[3,2,1-jk]-carbazol-11-one in 210 ml of warm methanol. The mixture was stirred overnight at room temperature. The suspension so obtained was then stirred for 1 hour at 0°–5° C. The solid substance was sucked off, washed with cold methanol, petroleum ether, and dried. Yield: 18.7 g.

The obtained salt was dissolved in 465 ml of dimethylformamide (DMF) while heating. An amount of 230 ml of warm water was added slowly, and the mixture absolute alcohol was added to a suspension of 7.8 g of the above obtained salt in 75 ml of absolute alcohol. The solution so obtained was evaporated almost to dryness under reduced pressure and at a temperature below 45° C. The residue was stirred into ethyl acetate. The solid substance was sucked off and washed with ethyl acetate. The solid substance was then stirred into isopropanol, sucked off, washed with isopropanol and with petroleum ether, and dried. Yield 3.6 g. Melting point: 226°–228° C. $[\alpha]_D^{25} = -5.0°$ (c=1.8; methanol).

EXAMPLE IV (+)-4,5,6,8,9,10-hexahydro-10-[(2-methyl-1H-imidazol]-1-yl)methyl]-11H-pyrido-[3,2,1-jk]-carbazol-11-one, hydrochloride In the same manner as described in Example III the isomer having the opposite rotation was obtained from 15.0 g of (R, S)-4,5,6,8,9,10-hexahydro-10-[(2-methyl-1H-imidazol-1-yl)methyl]-11H-pyrido-[3,2,1-jk]-carbazol-11-one, using 19.0 g of (−)-di-p-toluyl-L-tartaric acid monohydrate. Yield 4.15 g of the desired hydrochloride having a melting point of 223°–225° C. (decomposition), and $[\alpha]_D^{25} = +4.4°$ (c=1.7; methanol).

What is claimed is:
1. A compound of formula (2)

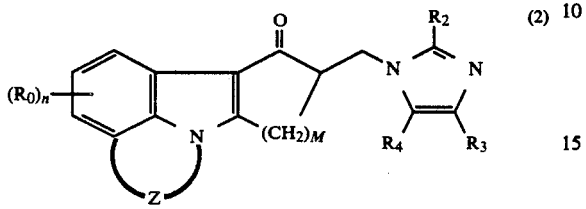

wherein $R_0$ is alkyl or alkoxy having 1–4 C-atoms, phenylalkoxy having 1–3 C-atoms in the alkoxy group, hydroxy, halogen, trifluoromethyl, trifluoromethoxy, trifluoromethylthio, or a group $R_7S(O)_p$, wherein $R_7$ is alkyl having 1–4 C-atoms and p has the value 0, 1 or 2, or $R_0$ is a group $R_8R_9N$, $R_8R_9N-CO-CH_2$— or $R_8R_9-N-CO$ wherein $R_8$ and $R_9$ are hydrogen or alkyl having 1–4 C-atoms and n has the value 0, 1 or 2, Z together with the carbon atom and nitrogen atom to which Z is bound and the intermediate carbon atom, forms a heterocyclic group consisting of 5–8 ring atoms in which, in addition to the nitrogen atom already present, a —CO— group or a second hetero atom from the group N, O, S, S-O or $SO_2$ may be present, which ring may be substituted with 1–3 alkyl groups having 1–4 C-atoms or a phenyl group, and m has the values 1–5, one of the groups $R_2$, $R_3$ and $R_4$ is hydrogen, alkyl having 1–6 C-atoms, cycloalkyl having 3–7 C-atoms, alkenyl having 2–6 C-atoms or phenylalkyl having 1–3 C-atoms in the alkyl group, and the two other groups independently of each other are hydrogen or alkyl having 1–6 C-atoms, or a pharmaceutically acceptable acid addition salt thereof.

2. A pharmaceutical composition comprising a pharmaceutically effective amount of a compound of claim 1 and a suitable liquid or solid carrier.

* * * * *

UNITED STATES PATENT AND TRADEMARK OFFICE
CERTIFICATE OF CORRECTION

PATENT NO.     : 4,939,136
DATED          : July 3, 1999
INVENTOR(S)    : Hans H. Haeck et al.

It is certified that error appears in the above-identified patent and that said Letters Patent is hereby corrected as shown below:

Title page,
Item [57], ABSTRACT,
Formula (2) should read as follows:

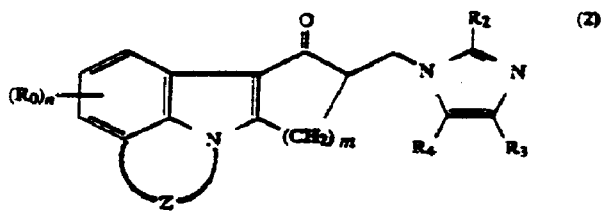

Column 1,
Formula (2) should read as follows:

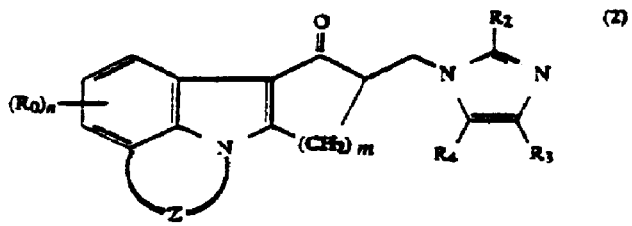

Columns 7-8,
The melting point of compound No. 17 should read as follows:

-- 159-161 --

UNITED STATES PATENT AND TRADEMARK OFFICE
CERTIFICATE OF CORRECTION

PATENT NO. : 4,939,136
DATED : July 3, 1999
INVENTOR(S) : Hans H. Haeck et al.

It is certified that error appears in the above-identified patent and that said Letters Patent is hereby corrected as shown below:

Column 9,
Formula (2) should read as follows:

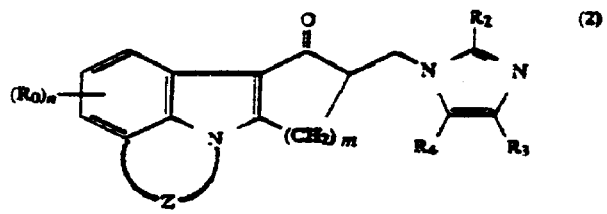

Signed and Sealed this

Eleventh Day of February, 2003

JAMES E. ROGAN
*Director of the United States Patent and Trademark Office*